United States Patent [19]

Kohno

[11] Patent Number: 5,182,004

[45] Date of Patent: Jan. 26, 1993

[54] FLOW-THROUGH TYPE HYDROGEN PEROXIDE ELECTRODE

[75] Inventor: Takeshi Kohno, Miyanohigashi, Japan

[73] Assignee: Horiba, Ltd., Kyoto, Japan

[21] Appl. No.: 437,346

[22] Filed: Nov. 15, 1989

[30] Foreign Application Priority Data

Dec. 10, 1988 [JP] Japan .......................... 63-160475[U]

[51] Int. Cl.⁵ ............................................. G01N 27/26
[52] U.S. Cl. ................................. 204/409; 204/153.12; 204/400; 204/403; 204/408; 204/435
[58] Field of Search .............. 204/400, 403, 408, 409, 204/415–420, 435, 153.12

[56] References Cited

U.S. PATENT DOCUMENTS

| | | | |
|---|---|---|---|
| 3,151,052 | 9/1965 | Arthur et al. | 204/409 |
| 3,367,849 | 2/1968 | Blaedel et al. | 204/409 |
| 3,434,953 | 3/1969 | Porter et al. | 264/408 |
| 3,510,421 | 5/1970 | Gealt | 204/409 |
| 3,526,577 | 9/1970 | Molloy | 204/415 |
| 3,556,950 | 1/1971 | Dahms | 204/420 |
| 3,770,607 | 11/1973 | Williams | 204/415 |
| 3,979,274 | 9/1976 | Newman | 204/415 |
| 4,452,682 | 6/1984 | Takata et al. | 204/415 |
| 4,589,958 | 5/1986 | Alexander et al. | 204/409 |
| 4,758,325 | 7/1988 | Kanno et al. | 204/418 |
| 4,791,932 | 12/1988 | Margules | 204/409 |
| 4,981,572 | 1/1991 | Easmunt et al. | 204/416 |

Primary Examiner—T. Tung
Attorney, Agent, or Firm—Price, Gess & Ubell

[57] ABSTRACT

An improved flow-through type electrode assembly includes an insulating transparent housing member having a transverse sample liquid passageway. A hollow cylindrical cathode forms a portion of the passageway and is physically displaced from a removable anode member that can be resiliently positioned in the passageway. A series of similar electrode assemblies can be interconnected together.

8 Claims, 3 Drawing Sheets

FLOW-THROUGH TYPE HYDROGEN PEROXIDE ELECTRODE

BACKGROUND OF THE INVENTION

1. Field of the Invention

The present invention relates to a flow-through type electrode assembly such as a hydrogen peroxide electrode, and more particularly, to an electrode construction of an improved configuration.

2. Description of Related Art

Flow-through type enzyme electrodes are known in the prior art as shown in FIG. 3. A sample liquid passage 32 is formed in a block member 31 of synthetic resins. An enzyme electrode 33 and a temperature compensating electrode 34 is disposed in the block number 31 so as to face the sample liquid passage 32. An upper space is provided above the enzyme electrode 33 and below a diaphragm 36 to provide an electrode reaction chamber 35 so that basic substances contained in the sample liquid flowing through the sample liquid passage 32 can be measured in a batch manner. This arrangement has been known as a so-called enzyme electrode (an electrode for measuring hydrogen peroxide and the like with enzymes as media), and is useful for measuring basic substances contained in a sample liquid.

The above-described enzyme electrode 33 can comprise an anode 38, shown in FIG. 4, formed of platinum and disposed almost at a center of an electrode body 37 formed of synthetic resins. A cathode 40 formed of a silver-silver chloride is disposed concentrically with the anode 38 extending through the cathode 40 and through an insulating layer 39. Both the anode 38 and the cathode 40 are advantageously integrally formed, and an enzyme-fixing membrane 41 extends over both the anode 38 and the cathode 40 and is fixed in position by an O-ring 41.

An enzyme electrode 33 having the above-described construction is characterized in that the desired basic substances can be measured by the use of a very small quantity of sample liquid. A disadvantage has occurred, however, in that when the volume of the electrode reaction portion 35 is increased, any small quantity of a basic substance contained within a small quantity of sample liquid is difficult to detect. If the electrode area (liquid-contacting area) of the anode 38 and cathode 40 are reduced in an effort to reduce the volume of the electrode reaction chamber 35, the liquid-contacting area of the anode 38, which is the working electrode, presents a limitation as to the amount of possible reduction in size. As a result, it is also difficult to detect basic substances contained in a very small quantity.

In addition, a disadvantage also occurs in a hydrogen peroxide electrode having almost the same construction as that of the above-described enzyme electrode 33, that is, a construction in which the enzyme-fixing membrane 38 is removed from the constituent members of the enzyme electrode 33. Thus, there is a need in the prior art to provide an improved electrode assembly that resolves the above problems.

SUMMARY OF THE INVENTION

The present invention has been achieved in view of the above-described problems in the prior art. Thus, it is an object of the present invention to provide a flow-through type of hydrogen peroxide electrode capable of obtaining a sufficiently large electrode output whereby basic substances contained in even a very small quantity of a sample can be surely detected.

In order to achieve the above-described object, a hydrogen peroxide electrode according to the present invention is characterized in that an anode and a cathode are arranged so as to communicate with a sample liquid passage formed in an electrode body under a condition wherein they are separated from each other and at least one element may form a portion of the liquid passageway. Additionally, one of the elements may be replaceable with a minimum of effort.

With the above-described construction, an electrode area of the anode, which is a working electrode, can be increased whereby a sufficiently large electrode output can be obtained. As a result, reliable detection can be achieved even for a very small quantity of a sample.

BRIEF DESCRIPTION OF THE DRAWINGS

One preferred embodiment of the present invention is shown in FIGS. 1 and 2, in which.

DESCRIPTION OF THE PREFERRED EMBODIMENTS

The following description is provided to enable any person skilled in the art to make and use the present invention and sets forth the best modes contemplated by the inventor of carrying out his invention. Various modifications, however, will remain readily apparent to those skilled in the art, since the generic principles of the present invention have been defined herein specifically to provide an improved electrode assembly that can be easily maintained in operation.

Figure 1:
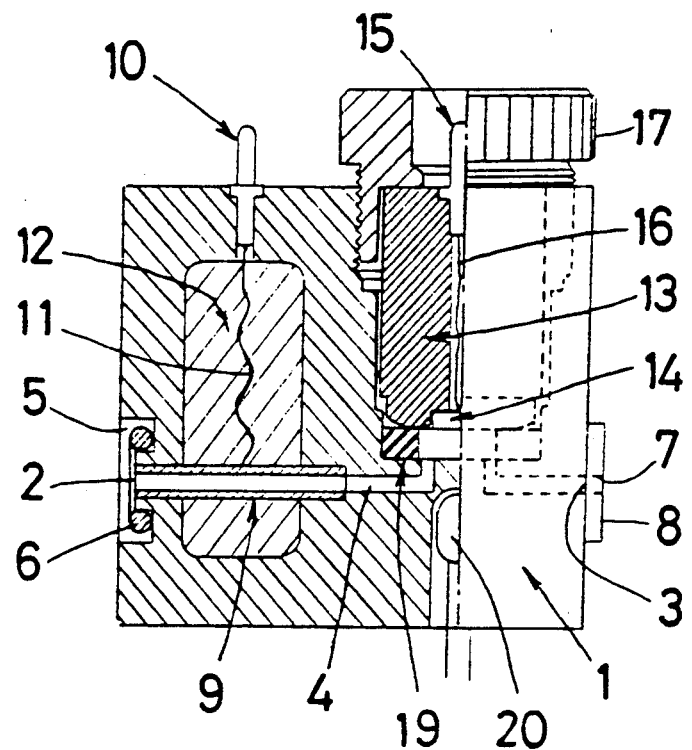
FIG. 1 is a longitudinal cross-sectional view showing one example of a flow-through type hydrogen peroxide electrode.
Figure 2:
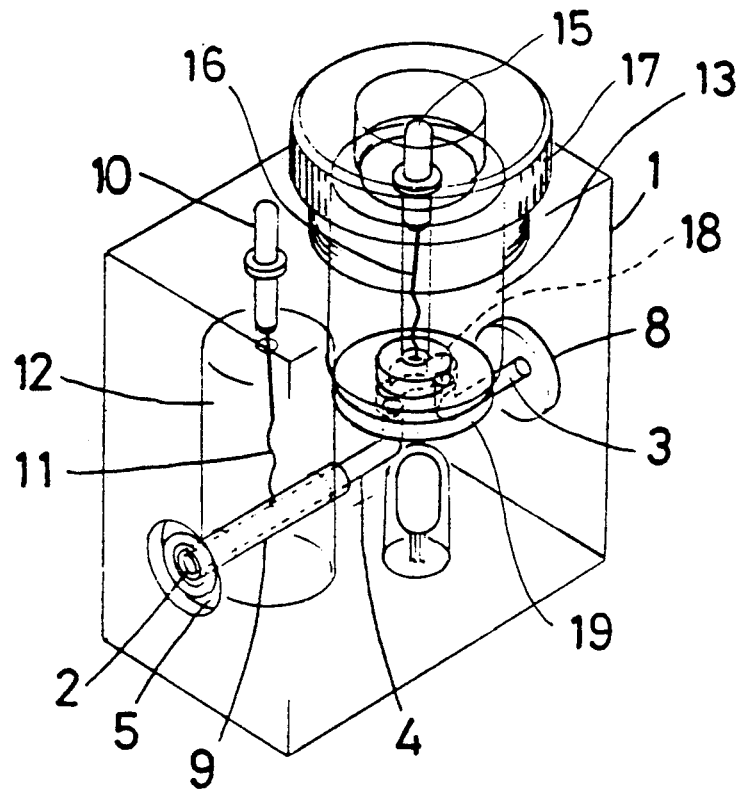
FIG. 2 is a perspective view of FIG. 1.
Figure 3:
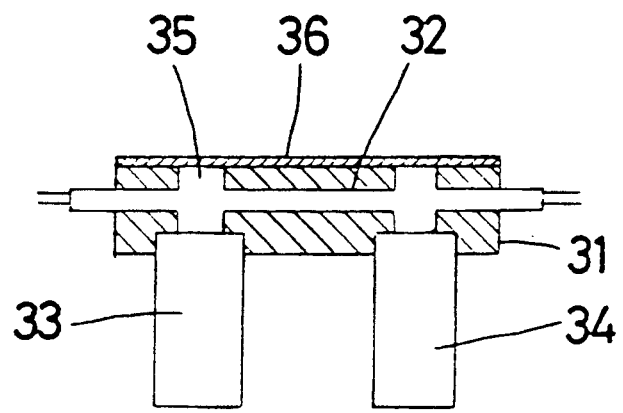
FIG. 3 is a longitudinal sectional view showing a prior art flow-through type enzyme electrode.
Figure 4:
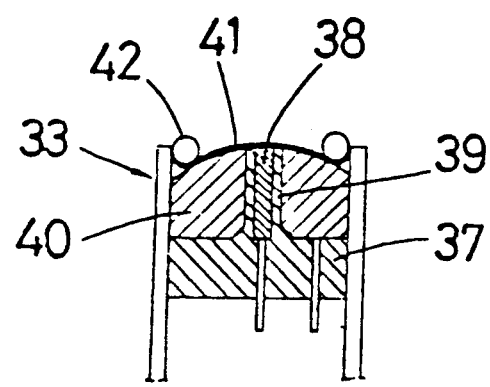
FIG. 4 is a longitudinal sectional view showing the principal parts of the prior art enzyme electrode shown in FIG. 3.

Referring now to FIGS. 1 and 2 showing one example of a flow-through type hydrogen peroxide electrode according to the present invention, reference numeral 1 designates a rectangular parallel piped or cubic electrode body formed of transparent synthetic resins, for example, acrylic resins. FIG. 1 is a cross-sectional view to illustrate the internal configuration. The electrode housing body 1 is provided with a sample liquid inlet port 2, which is opened at one end face thereof, a sample liquid outlet port 3 is opened at the other end face thereof opposite to port 2 and a sample liquid passage 4 (the construction will be described in detail later) connects the inlet port 2 with the outlet port 3.

Inlet port 2 is coaxial with a concave portion 5 of the electrode body 1 having a suitable depth and diameter around the inlet port 2. Reference numeral 6 designates an O-ring as a sealing member. In addition, the outlet port 3 is provided with a plug member 8 having a through hole at a height and diameter corresponding to the concave portion 5 and opened into the outlet port 3 so that a plurality of different electrode bodies 1 may be connected with each other under the condition that the sample liquid passages 4 of each electrode body will be closely connected with each other in series by inserting the plug member 8 into the concave portion 5 of another electrode body 1. Thus, the inlet port 2 and outlet port 3 provide complementary fasteners to enable a series of electrode assemblies to be connected together.

Reference numeral 9 designates a cylindrical hollow cathode positioned so as to form a part of the sample liquid passage 4 and, in particular, positioned to be opened into the inlet port 2. The cathode 9 is formed of, for example, a pipe formed of silver with its outside and inside surfaces plated with silver chloride. Reference numeral 10 designates a cathode terminal connected with the cathode 9 through a lead wire 11 for providing an output signal and reference numeral 12 designates silicon resins that secure the cathode pipe 9 and lead wire in the electrode body 1.

In order to provide the above-described cathode 9, a hole (not shown) having a predetermined size is formed in the electrode housing body 1 and the above-described cathode 9 is inserted into the hole through the inlet port 2. Subsequently, the cathode 9 is connected with the cathode terminal 10 via the lead wire 11 and the hole filed with silicon resins 12.

Reference numeral 13 designates a cylindrical insulating anode support body detachably provided in a threaded cavity which is opened into an upper portion of the electrode body 1 and formed of, for example, vinyl chloride resins or epoxy resins. The cavity or bore extends perpendicular to the passageway 4. The anode support body 13 is provided with a concave portion formed at an almost central position of a lower end face thereof. A cylindrical (having a diameter of, for example, 1 to 4 mm and a thickness of, for example, 1 mm) anode 14 having a surface subjected to a polishing process formed of platinum is fixed in the concave portion by means of, for example, resinous adhesives under a condition that a lower end face thereof is positioned on almost the same level as other portions of the lower end face of the anode support body 13.

Reference numeral 15 designates an anode terminal provided on a side (upper side) opposite to the anode 14 of the anode support body 13 and connected with the anode 14 through a lead wire 16 buried in the anode support body 13. In addition, reference numeral 17 designates a screw cap member for pressing the anode support body 13 downwards when threaded into the electrode body 1.

Furthermore, a rubber packing 19, which is provided with a hole 18 (this hole 18 forms a part of the sample liquid passage 4) having a shape of, for example,  as seen on a plan view hollowed out, is provided on the downstream side of the cathode 9 in the sample liquid passage 4, and the sample liquid passage 4 corresponding to the anode 14 has a shape of  as seen on a front view so that the anode support body 13 may be adjustably pressed down by screwing in a cap member 17 whereby the lower surface side of the anode 14 is pressed against the rubber packing 19 to face the hole 18.

The sample liquid passage 4 on the downstream side of the hole 18 is opened into the outlet port 3. Reference numeral 20 designates a temperature compensating thermistor.

With a flow-through type hydrogen peroxide electrode having the above-described construction, the anode 14, which is the working electrode, is arranged separately from the cathode 9, and both the anode 14 and the cathode 9 are arranged to be integral with the sample liquid passage 4, so that the liquid-contacting area of the anode 14 can be increased and, thus, a sufficiently large electrode output can be obtained.

In particular, since the cathode 9 is cylindrically formed in the above-described preferred embodiment, the internal surface area of the cathode 9 can be increased and, thus, an advantage occurs in that the liquid-contacting area of the cathode 9 can be increased with also a further subjective independent increase of the liquid-contacting area of the anode 14.

In addition, in the above-described preferred embodiment, since the anode body 13 provided with the anode 14 fixed therein is adapted to be detachably provided in the electrode body 1, the anode 14 can be simply maintained, inspected, and replaced, particularly with a transparent body 1. In the case where an enzyme-fixing membrane is disposed between the anode 14 and the packing 19 in the above-described flow-through type hydrogen peroxide electrode, it can be used as a flow-through type enzyme electrode, but it is preferable that a hydrophilic plastic film with enzymes, such as glucose-oxidase, alcohol oxidase, uricase, and glutamic acid oxidase, fixed thereon, be used as the enzyme-fixing membrane.

According to the present invention, since the anode and the cathode are arranged to be open to the sample liquid passage formed in the electrode body under a condition where they are separated from each other, the electrode area of the anode, which is the working electrode, can be increased and, thus, a sufficiently large electrode output can be obtained. As a result, reliable detection can be achieved even for a very small quantity of a sample. Additionally, a series of electrode assemblies can be easily ganged together because of the complementary locking feature of the inlet and outlet ports.

While the above embodiments have been disclosed as the best modes presently contemplated by the inventor, it should be realized that these examples should not be interpreted as limiting, because artisans skilled in this field, once given the present teachings, can vary from these specific embodiments. Accordingly, the scope of the present invention should be determined solely from the following claims.

What is claimed is:

1. An improved flow-through electrode assembly to directly position a cathode and anode electrode in contact with a sample liquid comprising:
   an electrode housing body having an inlet port and an outlet port with a sample liquid passageway extending therebetween;
   a cylindrical hollow metal cathode electrode positioned in the electrode body and forming a portion of said sample liquid passageway, only an interior portion of the cathode electrode being in liquid contact with the sample fluid;
   a disc anode electrode removably position in the electrode body at a position downstream of the cathode electrode with a surface of the anode electrode in liquid contact with the sample liquid;
   resilient means for resiliently mounting the anode electrode for sealing contact with the sample liquid passageway, and
   means for removably pressing the anode electrode against the resilient means, including
   a support member contacting the anode electrode, and
   force means on the electrode body for permitting an operator to progressively exert an increasing amount of force against the support member.

2. The improved flow-through electrode assembly of claim 1 wherein the electrode housing body is transparent.

3. The improved flow-through electrode assembly of claim 2 wherein the resilient means includes a packing member having a noncircular aperture that forms a portion of the sample liquid passageway.

4. The improved flow-through electrode assembly of claim 3, wherein the electrode housing body has a cavity extending transverse to the sample liquid passageway from a surface of the electrode housing body, intermediate the inlet body and the outlet port, the packing member is positioned at the bottom of the cavity and the support member is journalled in the cavity, and the force means for removably pressing the anode electrode includes a cap member with threads and corresponding threads in the cavity.

5. The improved flow-through electrode assembly of claim 4 further including a temperature compensating member positioned adjacent the anode electrode.

6. An improved flow-through electrode assembly to directly position a cathode and anode electrode in contact with a sample liquid comprising:
- a plastic transparent electrode housing body having an inlet port and an outlet port with a sample liquid passageway extending therebetween, and a cavity extending from, and transverse to, the sample liquid passageway from a surface of the electrode housing body, intermediate the inlet port and the outlet port;
- a cylindrical hollow metal cathode electrode positioned in the electrode body and forming a portion of said sample liquid passageway, only an interior portion of the cathode electrode being in liquid contact with the sample fluid;
- a support body removably mounted in the transverse cavity of the housing body;
- a disc anode electrode removably positioned in the electrode body at a position where the transverse cavity intersects the sample liquid passageway downstream of the cathode electrode with a surface of the anode electrode in liquid contact with the sample liquid, the support body having a lower surface configuration to receive and support the anode electrode;
- an electrical connector extending through the support body and connected to the anode electrode;
- resilient means positioned at the bottom of the transverse cavity for resiliently mounting the anode electrode to provide a sealing contact with the sample liquid passageway, and
- means for removably pressing the anode electrode against the resilient means by exerting a force on the support body.

7. The improved flow-through electrode assembly of claim 6 wherein an upper portion of the transverse cavity is threaded and a corresponding threaded cap member is threaded into the transverse cavity to exert said force on the support body.

8. The improved flow-through electrode assembly of claim 7 further including a temperature compensating member positioned adjacent the anode electrode.

* * * * *